US008883226B2

(12) United States Patent
Oh et al.

(10) Patent No.: US 8,883,226 B2
(45) Date of Patent: Nov. 11, 2014

(54) **PHARMACEUTICAL COMPOSITION FOR THE PREVENTION AND TREATMENT OF INFLAMMATORY DISEASE OR ASTHMA CONTAINING AN EXTRACT OF *DECASPERMUM FRUTICOSUM***

(75) Inventors: Sei Ryang Oh, Daejeon (KR); Kyung Seop Ahn, Daejeon (KR); Ok-Kyoung Kwon, Daejeon (KR); Hyeong Kyu Lee, Daejeon (KR); Joongku Lee, Daejeon (KR); Hyouk Joung, Daejeon (KR); Mee-Young Lee, Daejeon (KR); Hwa-Young Son, Daejeon (KR); Kyoung-youl Lee, Daejeon (KR); Sang Woo Lee, Daejeon (KR); Hang Jin, Yunnan (CN); Wan Yi Li, Yunnan (CN)

(73) Assignee: Korea Institute of Oriental Medicine, Daejeon (KR)

( * ) Notice: Subject to any disclaimer, the term of this patent is extended or adjusted under 35 U.S.C. 154(b) by 0 days.

(21) Appl. No.: 13/985,533

(22) PCT Filed: Feb. 7, 2012

(86) PCT No.: PCT/KR2012/000890
§ 371 (c)(1),
(2), (4) Date: Aug. 14, 2013

(87) PCT Pub. No.: WO2012/111934
PCT Pub. Date: Aug. 23, 2012

(65) Prior Publication Data
US 2013/0323331 A1    Dec. 5, 2013

(30) Foreign Application Priority Data
Feb. 16, 2011  (KR) .................. 10-2011-0013640

(51) Int. Cl.
*A61K 36/31*    (2006.01)
(52) U.S. Cl.
USPC .......................................... 424/725; 424/774
(58) Field of Classification Search
CPC .................................................... A61K 36/31
See application file for complete search history.

(56) References Cited

FOREIGN PATENT DOCUMENTS

JP    04128214 A   *  4/1992
JP    2001-220312 A    8/2013

OTHER PUBLICATIONS

Nials, A et al. Disease Models & Mechanisms; Nov.-Dec. 2008; 1:(4-5): 213-220.Mouse models of allergic asthma: acute and chronic allergen challenge.*
Persson, CGA. American Journal of Respiratory and Critical Care Medicine, 2002; 166: 6-8. Mice are not a good model of human airway disease.*
Wikipedia Contributors.Wikipedia, the free encyclopedia. "Alopecia areata". http://en.wikipedia.org/w/index.php?title=Alopecia_areata &printable=yes. Downloaded Jan. 11, 2014.*
International Search Report and Written Opinion of PCT/KR2012/000890 dated Feb. 7, 2012.
F.B. Ahmad et al; Traditional Medicinal Plants of Sabah, Malaysia Part III, The Rungus People of Kudat; International Journal of Pharmacognosy; vol. 33, No. 3, 1995; pp. 262-264.
L.Y. Chung et al; Central Nervous System Receptor Activities of Some Malaysian Plant Species; Pharmaceutical Biology, vol. 43; No. 3, 2005; pp. 280-288.
Nelson G.M. Gomes et al; Plants With Neurobiological Activity as Potential Targets for Drug Discovery; Progress in Neuro-Psychopharmacology & Biological Psychiatry: vol. 33, 2009; pp. 1372-1389.

* cited by examiner

*Primary Examiner* — Michele Flood
(74) *Attorney, Agent, or Firm* — Lucas & Mercanti, LLP

(57) ABSTRACT

A pharmaceutical composition for the prevention and treatment of inflammatory disease or asthma comprising the extract of *Decaspermum fruticosum* as an active ingredient. The extract of *Decaspermum fruticosum* of the present invention inhibited the increase of eosinophils in bronchoalveolar lavage fluid of the ovalbumin induced asthma animal model, had the activity of inhibiting the secretions of immunoglobulin and chemokine (Eotaxin) in bronchoalveolar lavage fluid and blood, and inhibited the secretions of NO and TNF-α in macrophages. Therefore, the extract of *Decaspermum fruticosum* of the present invention can be effectively used as an active ingredient of a pharmaceutical composition for the prevention and treatment of inflammatory disease or asthma, and of a health functional food for the prevention and improvement of inflammatory disease or asthma.

2 Claims, 7 Drawing Sheets

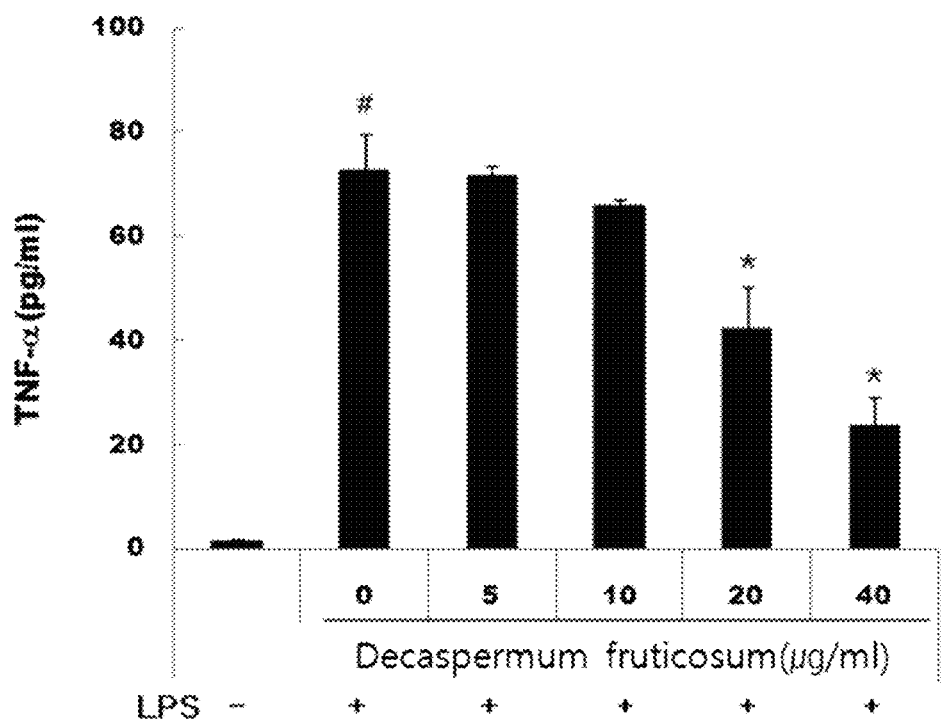

PHARMACEUTICAL COMPOSITION FOR THE PREVENTION AND TREATMENT OF INFLAMMATORY DISEASE OR ASTHMA CONTAINING AN EXTRACT OF *DECASPERMUM FRUTICOSUM*

CROSS-REFERENCE TO RELATED APPLICATIONS

This application is a 371 of PCT/KR2012/000890 filed on Feb. 7, 2012, which claims the priority of KR Application Serial No. 10-2011-0013640, filed Feb. 16, 2011, the contents of each of which are incorporated herein by reference.

BACKGROUND OF THE INVENTION

1. Field of the Invention

The present invention relates to a pharmaceutical composition for the prevention and treatment of inflammatory disease or asthma comprising the extract of *Decaspermum fruticosum* as an active ingredient.

2. Description of the Related Art

Inflammation is defined by the pathological state of abscess formed by the invasion of foreign source of infection such as bacteria, fungi, viruses, and other allergens. Particularly, when foreign bacteria invade in a specific tissue and proliferate therein, leukocytes recognize them and attack the proliferating bacteria actively. In the course, the dead leukocytes are accumulated in the tissue invaded by the bacteria along with the cell lysate resulted from the dead bacteria attacked by the leukocytes, leading to the formation of abscess. The treatment of abscess resulted from inflammation is focused on the anti-inflammation action. Anti-inflammatory action indicates the action inhibiting the proliferation of the invading bacteria using an anti-bacterial agent or the action promoting anti-inflammation by activating macrophages or increasing the functions of macrophages eating foreign materials accumulated in abscess to help the digestion and elimination of such invaders.

In general, inflammatory response is a defense mechanism for the recovery and regeneration of the tissues damaged by invasion causing structural changes, in which local blood vessels, various tissue cells, and immune cells are involved. The inflammatory response induced by the invasion of a foreign material is a normal defense mechanism to protect the living things. However, the inflammatory response induced abnormally or excessively can cause various diseases that are called inflammatory disease. Inflammatory disease is the disease that might put human in danger by amplifying or continuing inflammation with various inflammatory mediators secreted in target cells activated by external stimuli, which is exemplified by acute inflammation, joint disease including rheumatoid arthritis, skin disease including psoriasis, and allergic disease including bronchial asthma, etc.

Asthma is the disease characterized by bronchial hyper-sensitivity reacting to various stimuli, whose clinical symptoms are wheezing, dyspnea, and coughing caused by broad narrowness in the airway. In general, such symptoms can be improved naturally or by the treatment. In most cases, asthma is allergic reaction which is characterized by chronic airway inflammation and bronchial hyper-responsiveness (Minoguchi K and Adachi M. Pathophysiology of asthma. In: Cherniack N S, Altose M D, Homma I, editors. Rehabilitation of the patient with respiratory disease. New York: McGraw-Hill, 1999, pp 97-104).

Asthma is mainly divided into two groups, which are extrinsic asthma and intrinsic asthma. Extrinsic asthma develops symptoms by the exposure on allergens. Extrinsic asthma can be diagnosed when skin test or bronchial challenge test is positive on a certain allergen and is commonly observed in young age group. The major causes of extrinsic asthma are house dust and dust mites, and other minor causes are exemplified by pollen, animal epithelium, and fungi. Intrinsic asthma is induced or worsened by upper airway infection, exercise, anxiety, cold climate, and humidity change, which is usually observed among adults. There are examples of other asthma such as drug induced asthma, exercise induced asthma, and occupational asthma, etc.

Asthma is generally understood as a chronic inflammatory disease that is caused by the migration and infiltration of inflammatory cells in the airway and in tissues around the airway that have been proliferated, differentiated, and activated by interleukin-4, -5, and -13 produced by TH2 immune cells (Elias J A, et al., *J. Clin. Invest.*, 111, pp 291-297, 2003). In that case, activated inflammatory cells such as activated neutrophils, mast cells, and alveolar macrophages secrete various inflammatory mediators (cysteine, leukotriene, and prostaglandin) to play an important role in strong bronchoconstriction reaction (Maggi E., *Immunotechnology*, 3, pp 233-244, 1998; Pawankar R., *Curr. Opin. Allergy Clin. Immunol.*, 1, pp 3-6, 2001; Barnes P J, et al., *Pharmacol Rev.*, 50, pp 515-596, 1998).

The production of cytokines such as IL-4, IL-5 and IL-13, and immunoglobulin E involved in the activation of inflammatory cells and biosynthesis of cysteine leukotriene secreted in inflammatory cells including eosinophils mediated by the said production are key factors causing inflammation and allergic reaction that can be resulted in asthma. Therefore, attempts have been made to develop novel drugs to inhibit the production of cytokines and immunoglobulin E.

A variety of asthma drugs have been used nowadays but many of them have side effects that have to be carefully considered. Inhaling type corticosteroid is still the most important asthma treating drug with excellent effect. However, when the corticosteroid is used for a long term, serious side effects such as adrenal suppression, decreased bone mineral density, growth trouble, and complications in eyes and skin are developed. In a previous report, corticosteroid allegedly increases collagen synthesis (Warshmana G S, et al., *Am J Physiol* 274, 499-507, 1998). Even after many years of treatment with corticosteroid, the chance of normalization in bronchial hyper-responsiveness in chronic asthma patients is very rare. Long term administration of beta-2 agonist is not very effective in inhibiting airway remodeling, either (Jeffery P K, et al., *Am Rev Respir Dis* 145: 890-0, 1992). Continuous administration of beta-2 agonist such as salmeterol and formeterol can prevent asthma exacerbation but at the same time can cause death of asthma patient. Even though such side effects have been continuously reported, the drug has been still prescribed based on the belief that the asthma relieving effect is greater than the risk of side effects. The growth rate of children asthma patients who are relatively sensitive to side effects was measured. As a result, the growth rate of children asthma patients treated with oral leukotriene antagonist (montelukast) was greater by 1 cm/year than the growth rate of children asthma patients treated with inhaling type corticosteroid (Garcia Garcia ml, et al., *Pediatrics* 116(2): 360-9, 2005). If asthma is not treated properly in the growth period, not only the lung but also overall body growth can be inhibited or damaged. So, it is necessary to maintain normal healthy lung function with steady treatment. It has been confirmed to be more important to control inflammation in the airway by using a safe drug for the long term treatment. Thus, it is also important to consider the asthma relieving effect and side effects altogether before choosing an asthma treating drug. Leukotriene antagonist has been known to have low chances of side effects, so that it has been constantly prescribed for the prevention and long term treatment for asthma. However, asthma treating effect of it is weaker than other drugs, demonstrating only one third of asthma patients is improved. Therefore, it is still requested to develop a novel asthma treating agent that is safe without toxicity and does not cause drug resistance.

*Decaspermum fruticosum* is a short shrub having thin leaves facing each other. It has light pink flowers and purple fruits bearing lots of seeds. This shrub is widely distributed in Burma, Australia, and pacific islands. It flourishes in volcanic soils. Reports have already been made saying that a cosmetic composition comprising herb extract in addition to the extract of *Decaspermum fruticosum* can improve dry skin to be moisturized and creamy skin (Ohara, Mitsuharu & Hori, Michimasa, JP 2001220312). It has also been reported that young leaves and flower ear extracts of this shrub are effective in making hair grow and darker. However, the anti-inflammatory effect and anti-asthma effect of this plant have not been disclosed, yet.

The present inventors have tried to develop a novel drug to treat inflammatory disease or asthma using natural substances. As a result, the inventors confirmed that the extract of *Decaspermum fruticosum* reduced inflammatory cells, immunoglobulins, and chemokines in bronchoalveolar lavage fluid of airway-sensitized mouse model, and inhibited inflammatory response induced by lipopolysaccharide in vitro. The present inventors thus completed this invention by further confirming that the extract of *Decaspermum fruticosum* could be effectively used as an active ingredient of a preventive and therapeutic agent for inflammatory disease or asthma.

SUMMARY OF THE INVENTION

It is an object of the present invention to provide a composition for the prevention and treatment of inflammatory disease or asthma, and a health functional food comprising the extract of *Decaspermum fruticosum* as an active ingredient.

To achieve the above object, the present invention provides a pharmaceutical composition for the prevention and treatment of inflammatory disease comprising the extract of *Decaspermum fruticosum* as an active ingredient.

The present invention also provides a pharmaceutical composition for the prevention and treatment of asthma comprising the extract of *Decaspermum fruticosum* as an active ingredient.

The present invention also provides a health functional food for the prevention and improvement of inflammatory disease comprising the extract of *Decaspermum fruticosum* as an active ingredient.

The present invention also provides a health functional food for the prevention and improvement of asthma comprising the extract of *Decaspermum fruticosum* as an active ingredient.

The present invention also provides a treatment method for inflammatory disease containing the step of administering a pharmaceutically effective dose of the extract of *Decaspermum fruticosum* to a subject having inflammatory disease.

The present invention also provides a prevention method for inflammatory disease containing the step of administering a pharmaceutically effective dose of the extract of *Decaspermum fruticosum* to a subject.

The present invention also provides a treatment method for asthma containing the step of administering a pharmaceutically effective dose of the extract of *Decaspermum fruticosum* to a subject having asthma.

The present invention also provides a prevention method for asthma containing the step of administering a pharmaceutically effective dose of the extract of *Decaspermum fruticosum* to a subject.

The present invention also provides the extract of *Decaspermum fruticosum* for the use as a composition for the prevention and treatment of inflammatory disease.

The present invention also provides the extract of *Decaspermum fruticosum* for the use as a composition for the prevention and treatment of asthma.

The present invention also provides the extract of *Decaspermum fruticosum* for the use as a composition for a health functional food for the prevention and improvement of inflammatory disease.

In addition, the present invention provides the extract of *Decaspermum fruticosum* for the use as a composition for a health functional food for the prevention and improvement of asthma.

Advantageous Effect

As explained hereinbefore, the extract of *Decaspermum fruticosum* of the present invention not only reduced inflammatory cells, immunoglobulins and eotaxin in bronchoalveolar lavage fluid of the mouse whose airway was sensitized with ovalbumin but also suppressed asthma induced by the infiltration of such inflammatory cells and reduced the secretions of NO and TNF-α induced by such inflammatory factor as LPS as well. Therefore, the extract of *Decaspermum fruticosum* of the present invention can be effectively used as an active ingredient of a pharmaceutical composition for the prevention and treatment of inflammatory disease or asthma, and of a health functional food for the prevention and improvement of inflammatory disease or asthma.

BRIEF DESCRIPTION OF THE DRAWINGS

The application of the preferred embodiments of the present invention is best understood with reference to the accompanying drawings, wherein.

NC: the group not sensitized in the airway;

OVA: the group sensitized with ovalbumin in the airway;

Dex: the group treated with dexamethason at the concentration of 30 mg/kg;

DF-20: the group treated with the extract of *Decaspermum fruticosum* at the concentration of 20 mg/kg; and DF-40: the group treated with the extract of *Decaspermum fruticosum* at the concentration of 40 mg/kg.

Figure 2A:
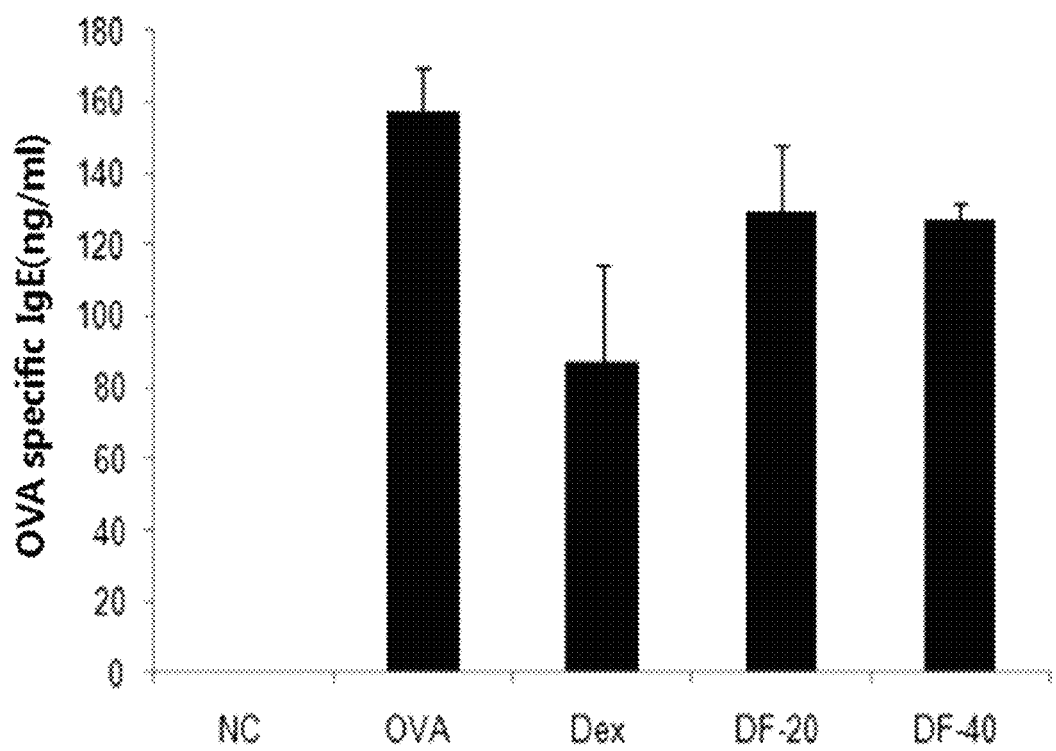

FIG. 2 is a set of graphs illustrating the effect of the extract of *Decaspermum fruticosum* on the immunoglobulin level in blood of the mouse whose airway was sensitized with ovalbumin:

FIG. 2a is a graph illustrating the effect of the extract of *Decaspermum fruticosum* on the IgE level in blood of the mouse whose airway was sensitized with ovalbumin;

NC: the group not sensitized in the airway;

OVA: the group sensitized with ovalbumin in the airway;

Dex: the group treated with dexamethason at the concentration of 30 mg/kg;

DF-20: the group treated with the extract of *Decaspermum fruticosum* at the concentration of 20 mg/kg; and DF-40: the group treated with the extract of *Decaspermum fruticosum* at the concentration of 40 mg/kg.

Figure 2B:
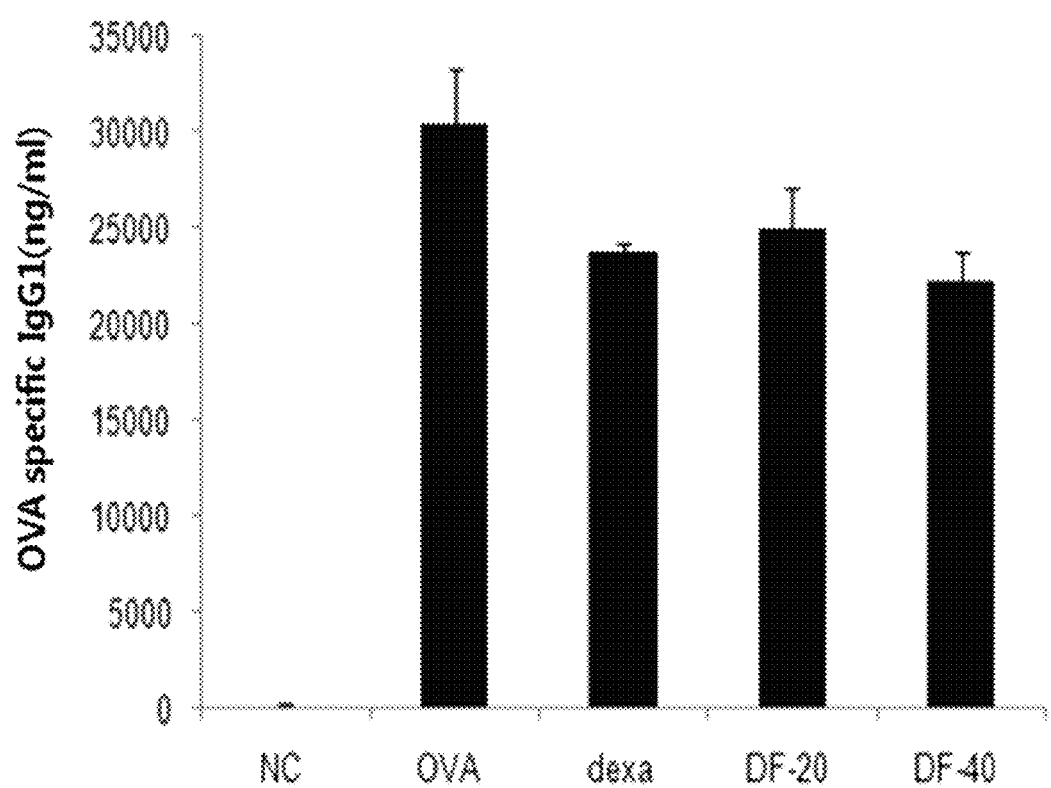

FIG. 2b is a graph illustrating the effect of the extract of *Decaspermum fruticosum* on the IgG1 level in blood of the mouse whose airway was sensitized with ovalbumin;

NC: the group not sensitized in the airway;

OVA: the group sensitized with ovalbumin in the airway;

Dex: the group treated with dexamethason at the concentration of 30 mg/kg;

DF-20: the group treated with the extract of *Decaspermum fruticosum* at the concentration of 20 mg/kg; and DF-40: the group treated with the extract of *Decaspermum fruticosum* at the concentration of 40 mg/kg.

Figure 3:
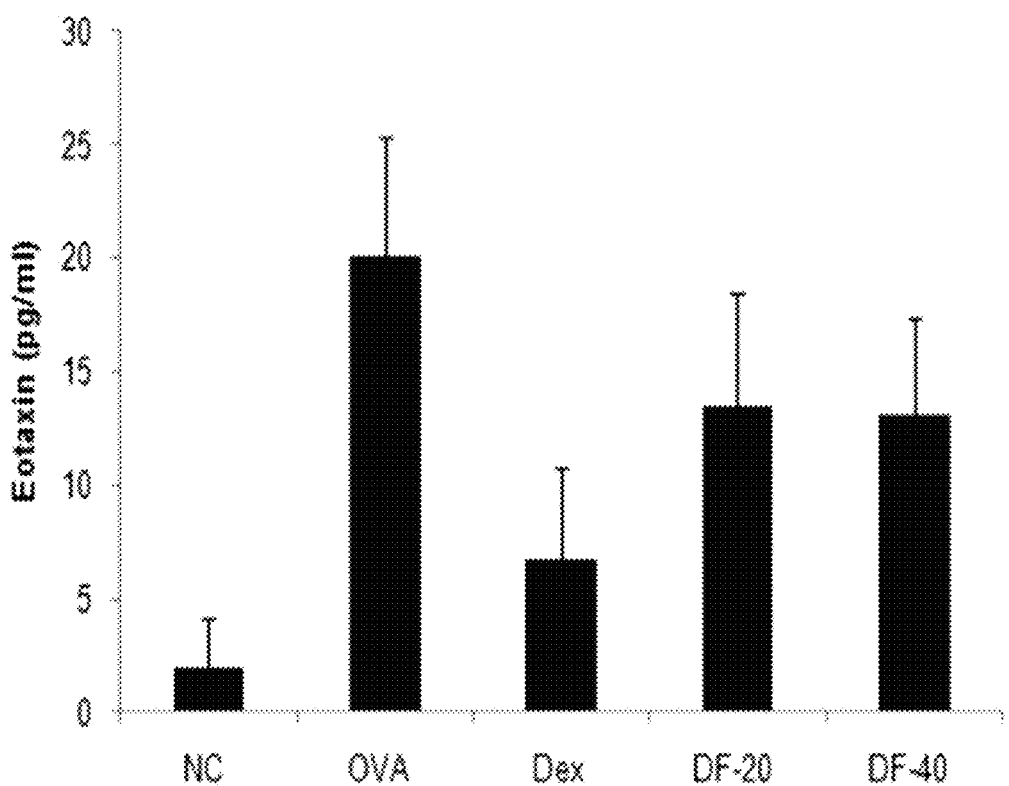

FIG. 3 is a graph illustrating the effect of the extract of *Decaspermum fruticosum* on the chemokine level in bronchoalveolar lavage fluid of the mouse whose airway was sensitized with ovalbumin:

NC: the group not sensitized in the airway;

OVA: the group sensitized with ovalbumin in the airway;

Dex: the group treated with dexamethason at the concentration of 30 mg/kg;

DF-20: the group treated with the extract of *Decaspermum fruticosum* at the concentration of 20 mg/kg; and DF-40: the group treated with the extract of *Decaspermum fruticosum* at the concentration of 40 mg/kg.

Figure 4:
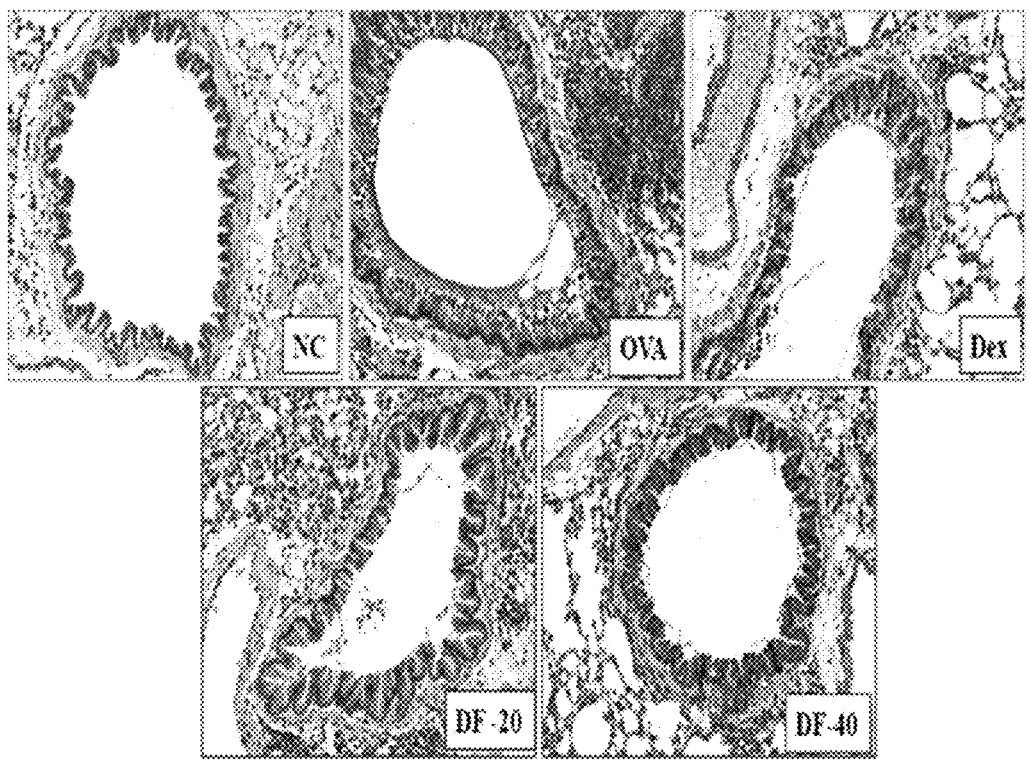

FIG. 4 is a graph illustrating the effect of the extract of *Decaspermum fruticosum* on the infiltration of inflammatory cells in airway mucosa of the mouse whose airway was sensitized with ovalbumin, confirmed by HE (hematoxylin-eosin) staining:

NC: the group not sensitized in the airway;

OVA: the group sensitized with ovalbumin in the airway;

Dex: the group treated with dexamethason at the concentration of 30 mg/kg;

DF-20: the group treated with the extract of *Decaspermum fruticosum* at the concentration of 20 mg/kg; and DF-40: the group treated with the extract of *Decaspermum fruticosum* at the concentration of 40 mg/kg.

Figure 5:
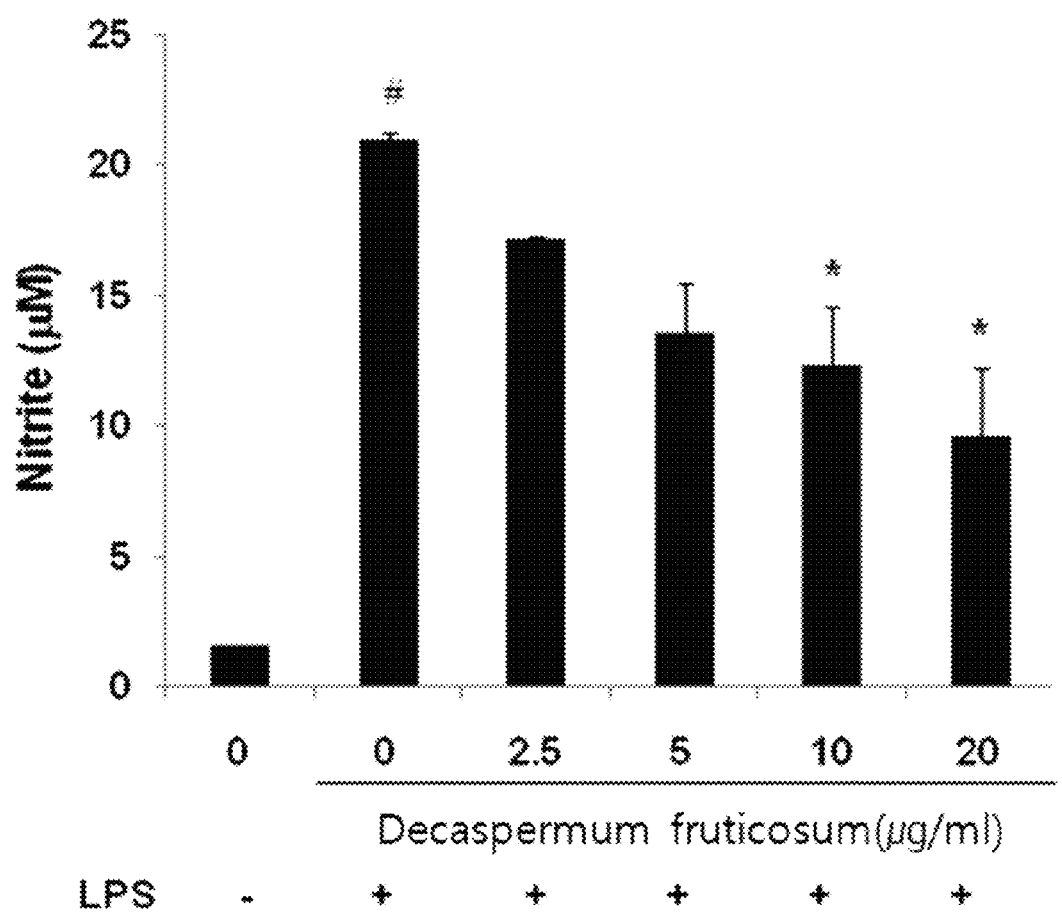

FIG. 5 is a graph illustrating the inhibitory effect of the extract of *Decaspermum fruticosum* on the NO generation induced by LPS in RAW264.7 cells:

*: $p<0.05$; and

: $p<0.005$.

FIG. 6 is a graph illustrating the inhibitory effect of the extract of *Decaspermum fruticosum* on the TNF-α generation induced by LPS in RAW264.7 cells:

*: $p<0.05$; and

: $p<0.005$.

DESCRIPTION OF THE PREFERRED EMBODIMENTS

Hereinafter, the present invention is described in detail.

The present invention provides a pharmaceutical composition for the prevention and treatment of inflammatory disease or asthma comprising the extract of *Decaspermum fruticosum* as an active ingredient.

The said inflammatory disease is preferably selected from the group consisting of dermatitis, allergy, atopy, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis of shoulder, tendinitis, tenosynovitis, peritendinitis, myositis, hepatitis, cystitis, nephritis, Sjogren's syndrome, multiple sclerosis, and acute and chronic inflammatory diseases, but not always limited thereto.

The extract of *Decaspermum fruticosum* is preferably prepared by the following steps, but not always limited thereto:

1) extracting *Decaspermum fruticosum* by using an extraction solvent;

2) filtering the extract of step 1);

3) concentrating the extract filtered in step 2) under reduced pressure; and 4) freeze-drying the concentrate obtained in step 3).

The *Decaspermum fruticosum* herein could be obtained from the cultivation or purchased on the market.

In the above method, the extraction solvent of step 1) is preferably selected from the group consisting of water, alcohol and the mixture thereof, or more preferably selected from the group consisting of $C_1$~$C_2$ lower alcohol and the mixture thereof, but not always limited thereto. At this time, the lower alcohol herein is preferably ethanol or methanol, but not always limited thereto. The volume of the extraction solvent is preferably 5~15 times the dried weight of *Decaspermum fruticosum*, and more preferably 7~10 times the weight, but not always limited thereto.

In the above method, the extraction method is selected from the group consisting of hot-water extraction, enfleurage, reflux extraction, and ultrasonification extraction, but not always limited thereto. In the above method, the preferable temperature for the extraction is 10° C.~100° C., and room temperature is more preferred. The extraction time is preferably 30 minutes~3 hours and more preferably 1~2 hours, but not always limited thereto. The extraction is preferably repeated 1~5 times and more preferably repeated 3 times, but not always limited thereto.

In the above method, the concentrating under reduced pressure of step 3) is preferably performed by using a rotary evaporator, but not always limited thereto. To dry the extract (step 4)), freeze-drying is preferably performed, but not always limited thereto.

In a preferred embodiment of the present invention, the bronchus of a mouse was sensitized with ovalbumin, to which the extract of *Decaspermum fruticosum* of the invention was treated. As a result, inflammatory cells such as eosinophils, neutrophils, lymphocytes, and macrophages in bronchoalveolar lavage fluid were reduced (see FIG. 1). In addition, immunoglobulin level in blood was also reduced by the administration of the extract of *Decaspermum fruticosum* dose-dependently (see FIG. 2). It was also confirmed that eotaxin, one of chemokines known to cause allergic disease, was down-regulated by the administration of the extract of *Decaspermum fruticosum* in bronchoalveolar lavage fluid of the mouse whose airway was sensitized with ovalbumin (see FIG. 3). Lung tissues of the mouse whose airway was sensitized with ovalbumin were also observed. As a result, the infiltration of inflammatory cells including eosinophils was observed in the lung tissue of the mouse sensitized with ovalbumin. However, the population of eosinophils was reduced in the lung tissues of the experimental group treated with the extract of *Decaspermum fruticosum* of the present invention (see FIG. 4).

In a preferred embodiment of the present invention, it was observed that the generations of NO and TNF-α known to be involved in inflammation induced by the treatment of lipopolysaccharide (LPS) which has been known to induce inflammation in vitro were reduced by the treatment of the extract of *Decaspermum fruticosum* of the present invention (see FIG. 5 and FIG. 6).

Therefore, the extract of *Decaspermum fruticosum* of the present invention can be effectively used as an active ingredient of a pharmaceutical composition for the prevention and treatment of inflammatory disease or asthma.

The composition of the present invention can be administered orally or parenterally (for example, application, intravenous, hypodermic, or peritoneal injection) but oral administration is preferred For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. The composition for local administration can be anhydrous or hydrous depending on the clinical prescription. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

Solid formulations for oral administration are powders, granules, tablets, capsules, soft capsules and pills. Liquid formulations for oral administrations are suspensions, solutions, emulsions, syrups and aerosols, and the above-mentioned formulations can contain various excipients such as wetting agents, sweeteners, aromatics and preservatives in addition to generally used simple diluents such as water and liquid paraffin.

The composition of the present invention can also include, in addition to the above-mentioned effective ingredients, one or more pharmaceutically acceptable carriers for the administration. The pharmaceutically acceptable carrier can be selected or be prepared by mixing more than one ingredients selected from the group consisting of saline, sterilized water, Ringer's solution, buffered saline, dextrose solution, maltodextrose solution, glycerol and ethanol. Other general additives such as anti-oxidative agent, buffer solution, bacteriostatic agent, etc., can be added. In order to prepare injectable solutions such as aqueous solution, suspension and emulsion, diluents, dispersing agents, surfactants, binders and lubricants can be additionally added.

The pharmaceutically acceptable additives are preferably included in the pharmaceutical composition of the present invention at the concentration of 0.1~90 weight part by the total weight of the composition, but not always limited thereto The effective dosage of the pharmaceutical composition of the present invention can be determined according to absorptiveness of the active ingredient, and age, gender and obesity of a patient by those in the art. In the case of oral administration, the pharmaceutical composition can be administered by 0.0001~100 mg/kg per day for an adult, and more preferably by 0.001~100 mg/kg per day. The administration frequency is once a day or a few times a day. The dosage cannot limit the scope of the present invention by any means.

The pharmaceutical composition for the prevention and treatment of inflammatory disease of the present invention can include, in addition to the extract of *Decaspermum fruticosum*, one or more effective ingredients having the same or similar function to the extract of *Decaspermum fruticosum*.

The pharmaceutical composition for the prevention and treatment of asthma of the present invention can include, in addition to the extract of *Decaspermum fruticosum*, one or more effective ingredients having the same or similar function to the extract of *Decaspermum fruticosum*.

The present invention also provides a health functional food for the prevention and improvement of inflammatory disease or asthma comprising the extract of *Decaspermum fruticosum* as an active ingredient.

In a preferred embodiment of the present invention, it was observed that the generations of NO and TNF-α known to be involved in inflammation induced by the treatment of lipopolysaccharide (LPS) which has been known to induce inflammation in vitro were reduced by the treatment of the extract of *Decaspermum fruticosum* of the present invention. Therefore, the extract of *Decaspermum fruticosum* of the present invention can be effectively used as an active ingredient of a health functional food for the prevention and improvement of inflammatory disease.

In a preferred embodiment of the present invention, the airway of a mouse was sensitized with ovalbumin, to which the extract of *Decaspermum fruticosum* of the invention was treated. As a result, the levels of inflammatory cells, immunoglobulins and eotaxin in bronchoalveolar lavage fluid were significantly reduced, compared with the control group not treated with the extract of *Decaspermum fruticosum*. Therefore, the extract of *Decaspermum fruticosum* of the present invention can be effectively used as an active ingredient of a health functional food for the prevention and improvement of asthma.

The extract of *Decaspermum fruticosum* herein is preferably extracted by using water, alcohol, or the mixture thereof as an extraction solvent. At this time, the alcohol herein is preferably $C_1$~$C_2$ lower alcohol, but not always limited thereto. The said inflammatory disease is preferably selected from the group consisting of dermatitis, allergy, atopy, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia (fibromyalgia), psoriatic arthritis, osteoarthritis, rheumatoid arthritis, periarthritis of shoulder, tendinitis, tenosynovitis, peritendinitis, myositis, hepatitis, cystitis, nephritis, Sjogren's syndrome, multiple sclerosis, and acute and chronic inflammatory diseases, but not always limited thereto.

The extract of *Decaspermum fruticosum* of the present invention can be provided as a food composition by mixing the extract with a sitologically acceptable carrier.

When the extract of *Decaspermum fruticosum* of the present invention is used for food or beverages, the extract of *Decaspermum fruticosum* can be added as it is or after being mixed with other food or ingredients, according to the conventional method.

The mixing ratio of the extract of *Decaspermum fruticosum* can be regulated according to the purpose of use (prevention, health enhancement or treatment).

If long term administration is required for health and hygiene or regulating health condition, the extract of *Decaspermum fruticosum* can be long-term administered since the extract of the present invention has been proved to be very safe.

The food herein is not limited. For example, the extract of *Decaspermum fruticosum* of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc.

The health beverages containing the extract of *Decaspermum fruticosum* of the present invention can additionally include various flavors or natural carbohydrates, etc, like other beverages. The natural carbohydrates above can be one of monosaccharides (ex: glucose, fructose, etc), disaccharides (ex: maltose, sucrose, etc), polysaccharides (ex: dextrin, cyclodextrin, etc) and sugar alcohols such as xilytole, sorbitol and erythritol. The content of the natural carbohydrate is preferably 1~20 g and more preferably 5~12 g per 100 g of the composition of the present invention. Besides, natural sweetening agents (ex: thaumatin, stevia extract, for example rebaudioside A, glycyrrhizin, etc.) and synthetic sweetening agents (ex: saccharin, aspartame, etc.) can be included as a sweetening agent.

In addition to the ingredients mentioned above, the food composition of the present invention can include a variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The food composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.001~50 weight part by the total weight of the composition of the invention.

The present invention also provides a treatment method for inflammatory disease containing the step of administering a pharmaceutically effective dose of the extract of *Decaspermum fruticosum* to a subject having inflammatory disease.

The present invention also provides a prevention method for inflammatory disease containing the step of administering a pharmaceutically effective dose of the extract of *Decaspermum fruticosum* to a subject.

The present invention also provides a treatment method for asthma containing the step of administering a pharmaceutically effective dose of the extract of *Decaspermum fruticosum* to a subject having asthma.

The present invention also provides a prevention method for asthma containing the step of administering a pharmaceutically effective dose of the extract of *Decaspermum fruticosum* to a subject.

In a preferred embodiment of the present invention, the bronchus of a mouse was sensitized with ovalbumin, to which the extract of *Decaspermum fruticosum* of the invention was treated. As a result, inflammatory cells such as eosinophils, neutrophils, lymphocytes, and macrophages in bronchoalveolar lavage fluid were reduced (see FIG. 1). In addition, immunoglobulin level in blood was also reduced by the administration of the extract of *Decaspermum fruticosum* dose-dependently (see FIG. 2). It was also confirmed that eotaxin, one of chemokines known to cause allergic disease, was down-regulated by the administration of the extract of *Decaspermum fruticosum* in bronchoalveolar lavage fluid of the mouse whose airway was sensitized with ovalbumin (see FIG. 3). Lung tissues of the mouse whose airway was sensitized with ovalbumin were also observed. As a result, the infiltration of inflammatory cells including eosinophils was observed in the lung tissue of the mouse sensitized with ovalbumin. However, the population of eosinophils was reduced in the lung tissues of the experimental group treated with the extract of *Decaspermum fruticosum* of the present invention (see FIG. 4).

In a preferred embodiment of the present invention, it was observed that the generations of NO and TNF-α known to be involved in inflammation induced by the treatment of lipopolysaccharide (LPS) which has been known to induce inflammation in vitro were reduced by the treatment of the extract of *Decaspermum fruticosum* of the present invention (see FIG. 5 and FIG. 6).

Therefore, the extract of *Decaspermum fruticosum* of the present invention can be effectively used for the prevention or treatment method for inflammatory disease or asthma.

The present invention also provides the extract of *Decaspermum fruticosum* for the use as a composition for the prevention and treatment of inflammatory disease.

The present invention also provides the extract of *Decaspermum fruticosum* for the use as a composition for the prevention and treatment of asthma.

The present invention also provides the extract of *Decaspermum fruticosum* for the use as a composition for a health functional food for the prevention and improvement of inflammatory disease.

In addition, the present invention provides the extract of *Decaspermum fruticosum* for the use as a composition for a health functional food for the prevention and improvement of asthma.

The extract of *Decaspermum fruticosum* of the present invention not only reduced inflammatory cells, immunoglobulins and eotaxin in bronchoalveolar lavage fluid of the mouse whose airway was sensitized with ovalbumin but also suppressed asthma induced by the infiltration of such inflammatory cells and reduced the secretions of NO and TNF-α induced by such inflammatory factor as LPS as well. Therefore, the extract of *Decaspermum fruticosum* of the present invention can be effectively used as an active ingredient of a pharmaceutical composition for the prevention and treatment of inflammatory disease or asthma, and of a health functional food for the prevention and improvement of inflammatory disease or asthma.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Extract of *Decaspermum fruticosum*

The present inventors purchased *Decaspermum fruticosum* from International Biological Material Research Center at Korea Research Institute of Bioscience and Biotechnology. To obtain the extract thereof, aerial part (leaves and stems) of *Decaspermum fruticosum* was taken and dried. 100 g of the dried sample was then pulverized, to which 800 ml of methanol was added, followed by extraction for 24 hours with refluxing at room temperature. The filtered supernatant was collected. This procedure was repeated twice to collect the supernatant. The obtained supernatant was concentrated under reduced pressure to give 2 g of the extract of *Decaspermum fruticosum*.

Experimental Example 1

Anti-Inflammatory Effect of the Extract of *Decaspermum fruticosum*

8-week old specific pathogen free female Balb/c mice (weight: approximately 20 g) were purchased from Orient Co. Ltd., Korea. 2 mg of aluminum hydroxide (Sigma A8222)

and 20 µg of ovalbumin (Sigma A5503) were suspended in 200 µl of PBS (pH 7.4), which was administered to each mouse by intraperitoneal injection twice at 2 weeks intervals for sensitization. On day 28, day 29, and day 30, PBS containing 1% ovalbumin was sprayed on the sealed cage where the mice stayed by using an ultrasonic sprayer for 20 minutes. The negative control group was composed of 6 mice having airways not sensitized. The positive control group was composed of 6 mice having airways sensitized with ovalbumin. The comparative group was composed of 6 mice treated with dexamethasone at the concentration of 30 mg/kg. The experimental group was composed of 6 mice orally administered with PBS containing 20 mg/kg or 40 mg/kg of the methanol extract of *Decaspermum fruticosum* one hour before antigen administration.

48 hours after the last antigen administration, excessive dose of pentobarbital (Sigma P3761) was administered to kill the animals, followed by tracheotomy. Bronchoalveolar lavage fluid (BALF) was collected from the trachea via cannula insertion method, 0.6 and at a time, three times, and then inflammatory cells and eosinophils were counted by the following method.

100 µl of the bronchoalveolar lavage fluid obtained from each group was loaded on the slide, followed by centrifugation using cytospin (Hanil Co., Korea) to fix the cells on the slide. The cells were stained with Trypan blue and counted by using a hemocytometer except the dead cells, which was repeated three times (Daigle I, et al., 2001).

The number of eosinophils was counted after staining with Diff-Quick reagent (Sysmex, Cat No. 38721, Switzerland), and the counting was performed by the same manner as described for the counting of the total cells above. Statistic analysis was performed by using Student's t-test and the significance was presented by p value.

Figure 1:
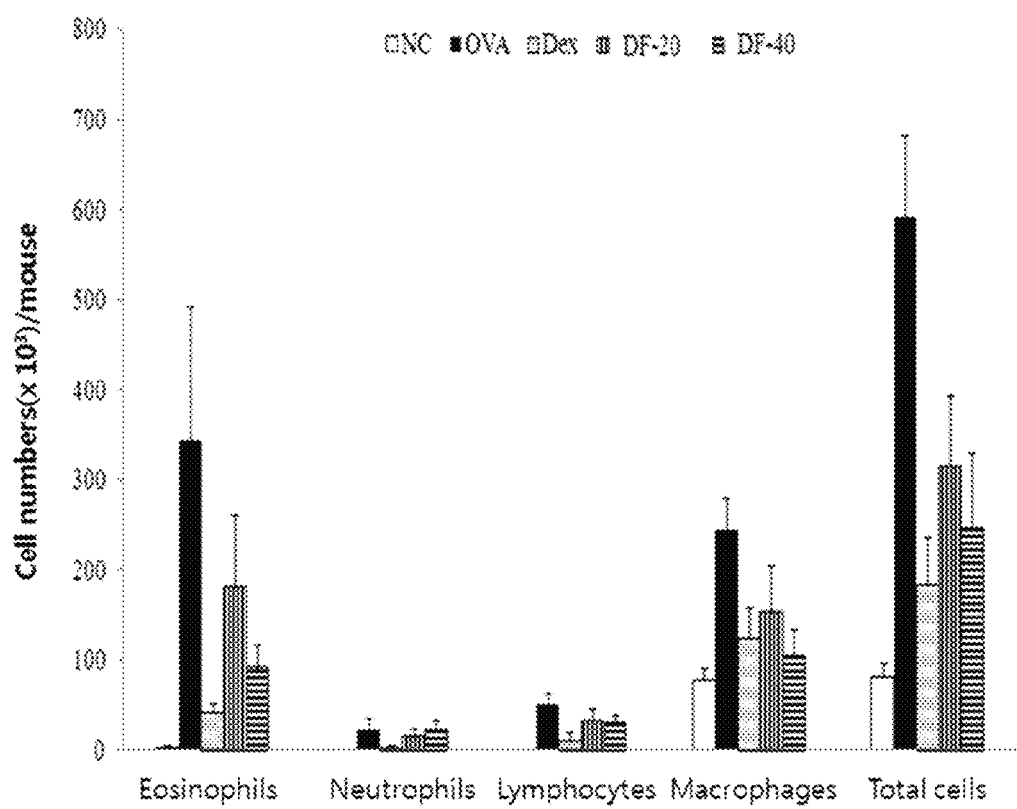
FIG. 1 is a graph illustrating the effect of the extract of *Decaspermum fruticosum* on eosinophils, neutrophils, lymphocytes, and macrophages in bronchoalveolar lavage fluid of the mouse whose airway was sensitized with ovalbumin.

As a result, as shown in FIG. 1, the mice of the positive control group which were sensitized with ovalbumin and administered with PBS demonstrated rapidly increased number of inflammatory cells, compared with the normal mice of the negative control group not sensitized. However, in the group treated with the extract of *Decaspermum fruticosum*, the increased numbers of inflammatory cells such as eosinophils, neutrophils, lymphocytes, and macrophages were all reduced by the treatment of the extract dose-dependently (FIG. 1).

Experimental Example 2

Effect of *Decaspermum fruticosum* Extract on Immunoglobulin Production

<2-1> Inhibitory Effect of *Decaspermum fruticosum* Extract on Immunoglobulin E (IgE) Production To measure the level of IgE in animal serum, the serum of each experimental group obtained in Experimental Example 1 was 40-fold diluted in dilute solution. 100 µl of the diluted solution was loaded in a 96-well plate in which 20 µg of ovalbumin used to induce asthma was attached, followed by inducing antigen-antibody reaction at room temperature for 2 hours.

As a result, as shown in FIG. 2a, it was confirmed that the level of IgE was rapidly increased in the mouse group sensitized with ovalbumin. In the meantime, the production of IgE was significantly inhibited in the group treated with the extract of *Decaspermum fruticosum*. This result was consistent with that of the positive control treated with dexamethasone known to have anti-inflammatory effect. Therefore, it was confirmed that the extract of *Decaspermum fruticosum* of the present invention efficiently inhibited ovalbumin-specific IgE production that plays a certain role in the mechanism causing allergic symptoms (FIG. 2a).

<2-2> Inhibitory Effect of *Decaspermum fruticosum* Extract on Immunoglobulin G1 (IgG1) Production To measure the level of IgG1 in animal serum, the serum of each experimental group obtained in Experimental Example 1 was 40-fold diluted in dilute solution. 100 µl of the diluted solution was loaded in a 96-well plate in which 20 µg of ovalbumin used to induce asthma was attached, followed by inducing antigen-antibody reaction at room temperature for 2 hours.

As a result, as shown in FIG. 2b, it was confirmed that the level of ovalbumin-specific IgG1 was rapidly increased in the mouse group sensitized with ovalbumin. In the meantime, the production of ovalbumin-specific IgG1 was significantly inhibited in the group treated with the extract of *Decaspermum fruticosum* of the present invention (FIG. 2b).

Experimental Example 3

Effect of *Decaspermum fruticosum* Extract on Chemokine

It has been well-known that Eotaxin gene supplements and activates CCR3 containing cells such as eosinophils, mast cells, and Th2 lymphocytes which play an important role in allergic diseases (Lilly, C. M. et al., *J. Allergy Clin. Immunol*, 108, 946-53, 2001). In this invention, the extract of *Decaspermum fruticosum* was treated to the mouse sensitized with ovalbumin, followed by measuring the content of eotaxin, one of chemokines, in bronchoalveolar lavage.

To measure the content of eotaxin, sandwich-type enzyme-linked immunosorbent assay (ELISA) was performed. Particularly, 100 µl of bronchoalveolar lavage fluid of each experimental group obtained in Experimental Example 1 was loaded in a 96-well plate in which cytokine antibody was attached, followed by inducing antigen-antibody reaction at room temperature for 2 hours. To measure the content of eotaxin, ELISA kit (BioSource International, Camarillo, Calif.) reacting to each cytokine specifically was used. The content of chemokine was measured according to the manufacturer's protocol.

As a result, as shown in FIG. 3, it was confirmed that the content of eotaxin was increased in the mouse group sensitized with ovalbumin. In the meantime, the content of eotaxin was reduced in the group treated with the extract of *Decaspermum fruticosum*, compared with the group treated with ovalbumin (FIG. 3). That is, the extract of *Decaspermum fruticosum* of the present invention can be effectively used for the allergic disease such as asthma (FIG. 3).

Experimental Example 4

Effect of *Decaspermum fruticosum* Extract on Inflammatory Cell Infiltration

The lung tissue of each experimental group of Example 1 was fixed in 10% neutral buffered formalin for 24 hours, followed by paraffin embedding. The embedded tissue was sliced into 4 mm sections, which were stained with hematoxylin and eosin Y (ThermoShandon, Pittsburgh, Pa.), followed by mounting on slides with Dako-mounting medium (Dakocytomation, Denmark). Upon completion of staining and mounting, the slides were examined under optical microscope.

As a result, as shown in FIG. 4, asthma was induced in alveoli and bronchioles of the mouse whose airway was sensitized with ovalbumin, compared with the control mouse whose airway was not sensitized. In addition, epithelial cells were injured and inflammatory cells including eosinophils were infiltrated into surroundings of the bronchioles in the sensitized mouse. In the meantime, the number of inflammatory cells including eosinophils was significantly reduced and epithelial cell damage was hardly observed in the mouse treated with the extract of *Decaspermum fruticosum*. The above result was consistent with the phenomenon that the inflammatory cells and eosinophils were reduced by the treatment of the extract of *Decaspermum fruticosum* as shown in Experimental Example 1 (FIG. 4).

Therefore, it was confirmed that the extract of *Decaspermum fruticosum* of the present invention inhibited asthma by reducing the infiltration of inflammatory cells including eosinophils and prevented epithelial cells from being damaged, so that it could be effectively used for the prevention or treatment of allergic disease caused by the infiltration of inflammatory cells.

Experimental Example 5

Inhibitory Effect of *Decaspermum fruticosum* Extract on NO Secretion in Macrophages The present inventors induced inflammation in Raw264.7 cells by treating LPS, and then measured the generation of inducible nitric oxide (NO) in order to evaluate the anti-inflammatory effect. Particularly, Raw264.7 cells were suspended in phenol-red free DMEM (Dulbecco's Modified Eagle Medium, Gibco) supplemented with FBS (10%) at the density of $5 \times 10^4$/ml. The cell suspension was inoculated in a 96-well plate. After 4 hours of attachment, the extract of *Decaspermum fruticosum* was treated at different concentrations, followed by culture for 1 hour. 1 μg/ml of lipopolysaccharide (LPS, Sigma) was treated thereto, followed by further culture for 24 hours. Upon completion of the culture, 100 μl of the supernatant was obtained, which was placed in a new 96-well plate. Griess reagent (Sigma) was added thereto by the equal volume, followed by reaction at room temperature for 10 minutes. Then, $OD_{550}$ was measured with a microplate reader (Bio-Rad).

NO production in the culture solution was measured using sodium nitrite standard curves prepared with different concentrations of sodium nitrite dissolved in the same medium. The amount of NO generated in the group treated with LPS was regarded as 100%, based on which the inhibitory rate of each sample was calculated by percentage. Statistic analysis was performed with Student's t-test and significance was presented with p value (*; $p<0.05$).

As a result, as shown in FIG. 5, the generation of NO was significantly increased in the group treated with LPS, compared with the negative control treated with an excipient. However, the generation of NO was significantly reduced in the group treated with the extract of *Decaspermum fruticosum*, compared with the group treated with LPS (FIG. 5).

Experimental Example 6

Inhibitory Effect of *Decaspermum fruticosum* Extract on TNF-α Production in Macrophages To investigate the inhibitory effect of the extract on inflammation increased intentionally by treating Raw264.7 cells with LPS, the present inventors measured the generation of TNF-α, one of inflammatory factors. Particularly, the level of TNF-α in the supernatant obtained in <Experimental Example 5> was measured by using TNF-α specific ELISA kit (BioSource International, Camarillo, Calif.) according to the manufacturer's protocol.

As a result, as shown in FIG. 6, the level of TNF-α was increased in the group treated with LPS, suggesting that inflammation was induced. However, the generation of TNF-α was reduced in the group treated with LPS and the extract of *Decaspermum fruticosum* of the present invention, dose-dependently (FIG. 6). That is, the extract of *Decaspermum fruticosum* of the present invention reduced the generation of inflammatory factor, proving that it could be effectively used for inflammatory disease.

The Manufacturing Examples of the composition for the present invention are described hereinafter.

Manufacturing Example 1

Preparation of Pharmaceutical Formulations

<1-1> Preparation of Powders

| | |
|---|---|
| Extract of *Decaspermum fruticosum* | 2 g |
| Lactose | 1 g |

Powders were prepared by mixing all the above components, which were filled in airtight packs according to the conventional method for preparing powders.

<1-2> Preparation of Tablets

| | |
|---|---|
| Extract of *Decaspermum fruticosum* | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Extract of *Decaspermum fruticosum* | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Extract of *Decaspermum fruticosum* | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Extract of *Decaspermum fruticosum* | 150 mg |
| Soybean extract | 50 mg |

| | |
|---|---|
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Foods

<2-1> Preparation of Snack and Flour Food 0.5~5.0 weight part of the extract of *Decaspermum fruticosum* of the present invention was added to the flour. Health enhancing foods such as bread, cake, cookies, crackers and noodles were prepared with the flour mixture according to the conventional method.

<2-2> Preparation of Dairy Products

5~10 weight part of the extract of *Decaspermum fruticosum* of the present invention was added to milk. Health enhancing dairy products such as butter and ice cream were prepared with the milk mixture according to the conventional method.

<2-3> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The extract of *Decaspermum fruticosum* of the present invention was concentrated under reduced pressure, hot-air dried and pulverized to obtain 60-mesh dry powders.

Sun-Sik was prepared by mixing the dry powders of the grains, seeds and the extract of *Decaspermum fruticosum* of the present invention according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Dry powders of the extract of *Decaspermum fruticosum* of the present invention (3 weight part),

*Ganoderma lucidum* (0.5 weight part),

*Rehmannia glutinosa* (0.5 weight part)

Manufacturing Example 3

Preparation of Beverages

| | |
|---|---|
| Extract of *Decaspermum fruticosum* | 1000 mg |
| Citric acid | 1000 mg |
| Oligosaccharide | 100 g |
| Maesil (*Prunus mume*) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

As explained hereinbefore, the extract of *Decaspermum fruticosum* of the present invention has the inhibitory effect on asthma and inflammation, so that it can be effectively used for the preparation of a pharmaceutical composition for the prevention and treatment of inflammatory disease or asthma, and of a health functional food for the prevention and improvement of inflammatory disease or asthma.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method of treating asthma in a human in need thereof comprising administering to said human a therapeutically effective amount of an extract of *Decaspermum fruticosum*, wherein the extract is at least one solvent selected from the group consisting of water and a $C_1$ to $C_2$ lower alcohol or a mixture thereof to treat the asthma in said human.

2. The method according to claim 1, wherein the $C_1$ to $C_2$ lower alcohol is ethanol or methanol.

\* \* \* \* \*